US008246695B2

(12) United States Patent
Mosler

(10) Patent No.: US 8,246,695 B2
(45) Date of Patent: Aug. 21, 2012

(54) ARTIFICIAL FOOT

(75) Inventor: Lueder Mosler, Duderstadt (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 98 days.

(21) Appl. No.: 11/570,683

(22) PCT Filed: Jun. 28, 2005

(86) PCT No.: PCT/DE2005/001156
§ 371 (c)(1),
(2), (4) Date: Sep. 7, 2007

(87) PCT Pub. No.: WO2006/000211
PCT Pub. Date: Jan. 5, 2006

(65) Prior Publication Data
US 2008/0004718 A1    Jan. 3, 2008

(30) Foreign Application Priority Data
Jun. 29, 2004    (DE) .......................... 10 2004 031 562

(51) Int. Cl.
*A61F 2/66* (2006.01)
(52) U.S. Cl. ............................... 623/55; 623/53; 623/47
(58) Field of Classification Search ................ 623/47–56
See application file for complete search history.

(56) References Cited

U.S. PATENT DOCUMENTS

| | | | | |
|---|---|---|---|---|
| 2,475,372 A | * | 7/1949 | Catranis | 623/49 |
| 2,475,373 A | | 7/1949 | Catranis | |
| 2,749,557 A | * | 6/1956 | Riddle | 623/50 |
| 4,958,705 A | | 9/1990 | Horvath | |
| 5,571,205 A | * | 11/1996 | James | 623/24 |
| 5,913,902 A | | 6/1999 | Geible et al. | |
| 6,007,582 A | * | 12/1999 | May | 623/55 |
| 6,099,572 A | * | 8/2000 | Mosler et al. | 623/53 |
| 6,443,993 B1 | * | 9/2002 | Koniuk | 623/24 |
| 6,767,370 B1 | * | 7/2004 | Mosler et al. | 623/55 |
| 6,855,170 B2 | * | 2/2005 | Gramnas | 623/49 |
| 7,520,904 B2 | * | 4/2009 | Christensen | 623/47 |
| 2002/0138153 A1 | * | 9/2002 | Koniuk | 623/24 |
| 2003/0045944 A1 | | 3/2003 | Mosler et al. | |
| 2004/0186590 A1 | * | 9/2004 | Townsend et al. | 623/38 |
| 2008/0306612 A1 | * | 12/2008 | Mosler | 623/55 |

FOREIGN PATENT DOCUMENTS

| | | |
|---|---|---|
| DE | 303 735 C | 5/1916 |
| DE | 309 066 C | 11/1917 |
| DE | 100 10 302 A1 | 9/2001 |
| FR | 528 796 A | 11/1921 |
| RU | 2 196 547 C2 | 1/2003 |
| RU | 2 198 628 C2 | 2/2003 |
| WO | WO 92/20305 | 11/1992 |

* cited by examiner

*Primary Examiner* — William H Matthews
*Assistant Examiner* — Marcia Hoffman
(74) *Attorney, Agent, or Firm* — Whitham Curtis Christofferson & Cook, PC.

(57) ABSTRACT

An artificial foot has a connecting part for a lower leg part, and a base foot part rotatably connected to the connecting part via an ankle joint. The base foot part extends rearwards of the ankle joint in a heel section and forwards of the ankle joint in a midfoot section. A forefoot part is rotatably connected to the midfoot section. In order to allow an automatic adaptation of the foot to varying heel heights while ensuring a good stability, an articulated connection transmits the angular position of the connecting part in relation to the base foot part in a proportional manner to the angular position of the forefoot part in relation to the base foot part.

16 Claims, 12 Drawing Sheets

ARTIFICIAL FOOT

FIELD OF THE INVENTION

The invention relates to an artificial foot with a connecting part for a lower leg part, with a base foot part which is pivotably connected to the connecting part via an ankle joint and extends rearward of the ankle joint into a heel section and forward of the ankle joint into a midfoot section, and with a forefoot part connected pivotably to the midfoot section.

BACKGROUND

An artificial foot of this kind is known from U.S. Pat. No. 5,913,902. The ankle joint is located in the axis of a tubular lower leg part of a below-knee prosthesis received by an adapter piece of the connecting part. The ankle joint and the joint between forefoot part and base foot part are pivotable independently of one another, the pivotability being elastically damped by compression springs fitted between the respective joint parts. This foot construction permits the use of the artificial foot with several heel heights, since the foot can be adapted to different angles of the forefoot and of the connecting part relative to the base foot part. However, the static arrangement in this case alters as a function of the heel height, so that widely different walking dynamics arise also as a function of the heel height.

DE 100 10 302 A1 discloses a prosthetic foot with a movable ankle joint and with a similarly movable forefoot part. The object of the disclosed foot construction is to substantially prevent dropping of the knee joint, and thus of the hip joint, during heel-to-toe movement across the toe area. To achieve this, a plantar flexion is sought between foot and lower limb, that is to say between base foot part and connecting part. For this purpose, a coupling rod is secured between the forefoot part and the base foot part, the securing in the base foot part being effected by an oblong hole. One end of the coupling rod protrudes into the area of the connecting part and, because of the bending of the forefoot part, limits the angle between connecting part and base foot part. By limiting the angle, further dropping of the knee, and thus of the hip, is avoided. Adaptation of the foot to different heel heights is neither provided for nor indeed possible in the described construction.

Prostheses are known in which the sagittal adaptation of the prosthetic foot can be done by the patient, in order to permit adaptation to different heel heights. A wrong adjustment cannot be ruled out. To ensure that the forefoot can adapt to the shape of the shoe, it is made soft. As a result, however, the load uptake in the forefoot area at the end of the stance phase is insufficient.

SUMMARY

The object of the present invention is to design an artificial foot of the aforementioned type in such a way that it can automatically adapt to different heights of shoe heel and, in so doing, guarantees good stability in a standing position.

In an artificial foot of the type mentioned at the outset, this object is achieved, according to the invention, by an articulated connection which transmits the angular position of the connecting part relative to the base foot part in a proportional manner to the angular position of the forefoot part relative to the base foot part.

The foot according to the invention thus provides for a forced coupling between the connecting part and the forefoot part in respect of the angular position relative to the base foot part. According to this forced coupling, a change in the angular position of the connecting part in a rearward direction leads to a proportional lifting of the forefoot part. If the artificial foot, starting from a position without heel (barefoot position), is inserted into a shoe with a high heel, the position of the lower leg (and thus of the connecting part) relative to the base foot part changes in the sense of a rearward shifting of the angle. Accordingly, the forefoot part is lifted until it again lies parallel to the contact surface (front sole of the shoe). It is therefore not necessary for the forefoot part to be made soft so that the forefoot part lies firmly on the supporting surface and thus takes up the required load for a secure stance, even with a high heel.

The articulated arrangement is in this case a multiple-joint arrangement and can in particular be a four-joint arrangement.

The articulated connection is preferably formed by the midfoot section and by a linking rod that is connected in an articulated manner to forefoot part and connecting part, these elements then being disposed in a four-joint or multiple-joint arrangement, wherein the midfoot section and linking rod can lie substantially parallel to one another.

In a preferred embodiment of the invention, the connecting part is provided with an extension piece which extends downward across the ankle joint and on which the linking rod is secured pivotably via one of its free ends.

The articulated connection according to the invention can be formed by pivot joints, but also by material hinges, said material hinges being formed by a flexible section of a coupling piece of the articulated connection.

The function of the artificial foot according to the invention entails the base foot part being designed as a rocker which is mounted more or less centrally between the heel and the area of the ball of the foot. The prosthetic foot thus generates a structure that allows the loading line to extend at all times through the bearing point of the rocker. This corresponds to the circumstances of the natural foot. By virtue of the coupling between the connecting part and the forefoot part, the forefoot always extends approximately parallel to the ground. This corresponds to the design of shoes with a constant sole thickness in this area, which is necessary, since otherwise the foot would be pressed into the point of the shoe.

If the foot according to the invention is constructed only with rigid elements, it very quickly generates, in the middle of the standing phase, a forefoot resistance that does not correspond to the feeling when standing on a natural foot. To permit adaptation to the natural feeling when standing, it is advantageous for at least one coupling piece of the articulated arrangement to be elastically deformable in the longitudinal direction. This is particularly expedient for a coupling piece that is subjected predominantly to tensile loading in the articulated arrangement. In this case, the coupling piece can be designed as a curved leaf spring which initially responds gently to tension and then gradually increases the stiffness.

Further possible improvements are obtained in respect of the dynamics of walking. When the heel touches down during walking, the base foot part designed according to the invention as a rocker tilts forward, as a result of which the connecting part is inclined relatively rearward and, consequently, the forefoot part is drawn upward. If one wishes to avoid this effect, a distinction has to be made between a momentary, substantial loading of the heel section of the base foot part when the heel touches down during walking, and the longer-term loading for adaptation of the height of the heel. This can be achieved by providing an adjustment element for the angle between base foot part and connecting part, which adjustment element becomes effective only when there is a load that continues for several seconds. An adjustment element of this kind can be a hydraulic cylinder. The latter is expediently combined with an elastic member that is deformable under momentary loading (when the heel touches down), in order to achieve a cushioning action when the heel touches down during walking.

The distinction between momentary loading when the heel touches down and long-term adaptation of the height of the heel can preferably be achieved by a valve arrangement being inserted into a circuit path of the hydraulic cylinder, which valve arrangement interrupts the flow of the hydraulic fluid in the circuit path when the flow velocity suddenly increases. By contrast, in the case of a slow adaptation, the valve arrangement does not shut the circuit, so that the hydraulic fluid is able to flow through for changing the adjustment element formed by the hydraulic cylinder.

During the walking process, the foot normally rolls forward across the forefoot area. In doing so, the lower leg (the connecting part) is tilted forward relative to the base foot part, so that the coupling according to the invention leads to a pressing down of the forefoot part, that is to say the forefoot "digs in". This can be alleviated by designing the articulated connection so as to have a reduced transmission factor in respect of the angular positions. However, this also impairs the adaptation to the different heel heights.

It is therefore preferred that at least one coupling piece of the articulated arrangement is designed to be adjustable in length, the length adjustment being able to be controlled by at least one sensor that detects parameters of the walking or standing situation. The length adjustment can be performed by a hydraulic cylinder.

It is in each case expedient to arrange an elastic member between forefoot part and base foot part, which elastic member permits in particular the length adjustment of a coupling piece, in particular of the linking rod.

The elastic design of the linking rod can be supplemented or replaced by an elastic design of the extension piece of the connecting part on which the linking rod is articulated. The extension piece itself can be made of an elastic material or can be connected pivotably and in an elastic manner to the rest of the body of the connecting part.

It is particularly expedient, for the present invention, if the ankle joint is arranged at a distance forward of an adapter attachment on the connecting part receiving the lower leg part. Good stability is thus achieved, and the necessary torques for controlling the foot are applied.

DESCRIPTION OF THE DRAWINGS

The invention will be explained in more detail below on the basis of illustrative embodiments depicted in the drawing, in which.

DETAILED DESCRIPTION

Figure 1:
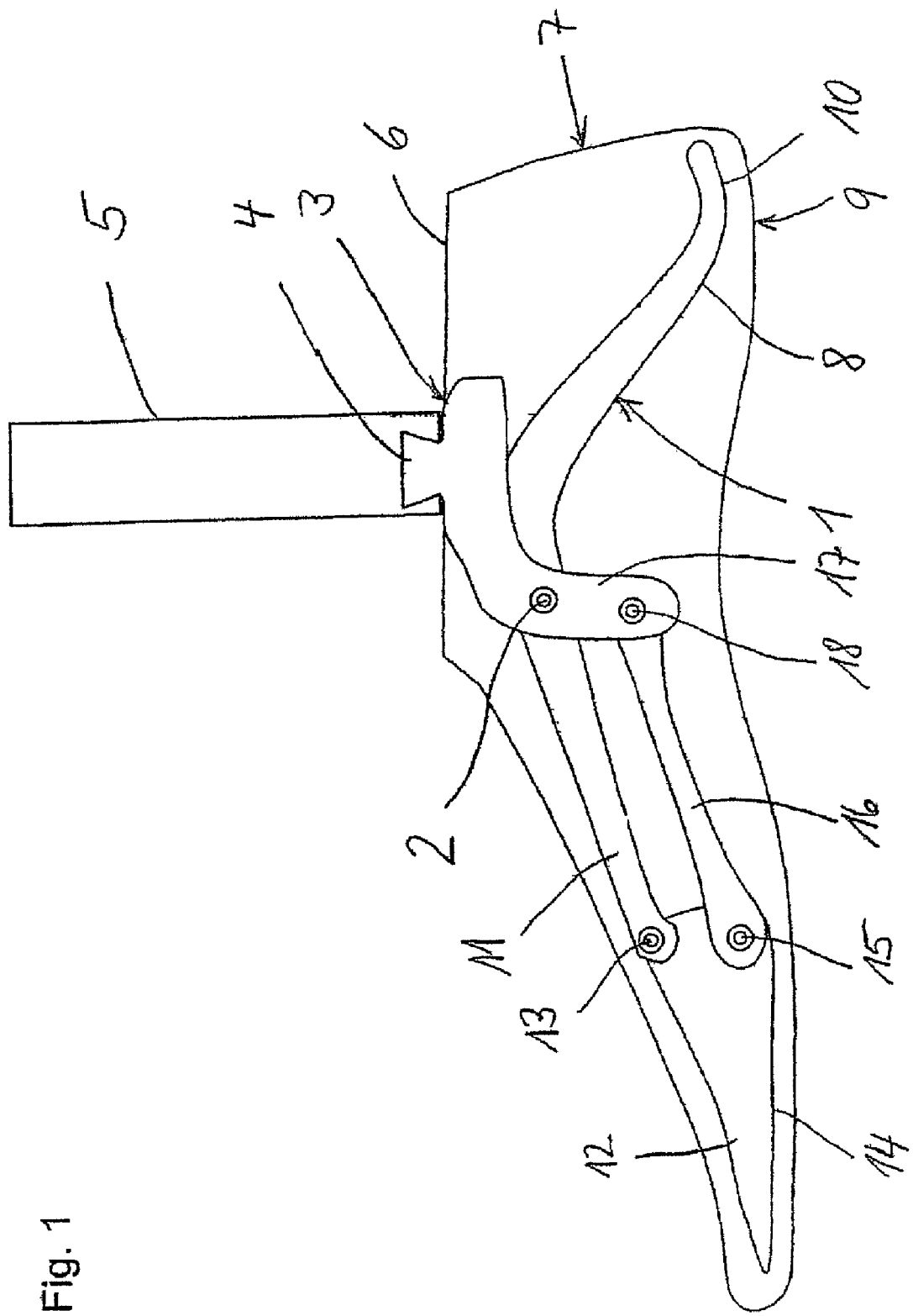
FIG. 1 shows the basic structure of an artificial foot according to a first embodiment, depicted in the barefoot state.

A first embodiment of a foot according to the invention is shown schematically in FIGS. 1 to 5. The basic structure of the foot includes a base foot part 1, which is connected to a connecting part 3 via an ankle joint 2 designed as a pivot joint. The connecting part 3 has an adapter attachment 4 in the form of an upturned truncated cone which is used to receive, in an adjustable manner, a tubular lower leg part 5 of a below-knee prosthesis. The adapter attachment 4 thus protrudes from an upper delimiting surface 6 of a cosmetic cover 7 of the foot prosthesis which encloses the functional parts of the foot prosthesis up to the end face 6.

The base foot part 1 forms, rearward of the ankle joint 2, a heel section 8 which slopes rearward and downward from the connecting part 3 and ends in a heel contact surface 10 close to the sole 9 of the cosmetic cover 7. The base foot part 1 extends forward of the ankle joint 2 in a substantially rectilinear midfoot section 11, on the front end of which a forefoot part 12 representing the toe area is articulated via a pivot joint 13. The forefoot part 12 forms an approximately triangular wedge whose underside 14 lies parallel to the sole 9 of the cosmetic cover 7 in the area of the forefoot 12. The pivot joint 13 is located at the upper tip of the triangular forefoot part 12. In the lower area of the triangular forefoot part 12 there is a further pivot joint 15 via which the forefoot part 12 is connected by means of a linking rod 16 to the connecting part 3. For this purpose, the connecting part 3 has a downwardly extending and rigid extension piece 17 on which there is a pivot joint 18 for securing the linking rod 16. The connecting part 3 is therefore L-shaped, with a horizontal branch lying approximately parallel to the end face 6, and, arranged approximately at right angles to the latter, a downwardly extending branch in the form of the extension piece 17.

The axes of the pivot joints 2, 13, 15, 18 lie parallel to one another and transverse to the sagittal plane of the foot, that is to say parallel to the frontal plane of the patient. In the first embodiment shown, the spacings between the pivot joints 13, 15, on the one hand, and 2, 18, on the other, are approximately the same, so that the midfoot section 11 and the linking rod 16 are oriented approximately parallel to one another (with respect to the connection line between the pivot joints 2, 13, on the one hand, and 15, 18 on the other). In the embodiment shown, the articulated connection between the connecting part 3 and the forefoot part 12 thus corresponds to a parallelogram linkage.

Figure 2:
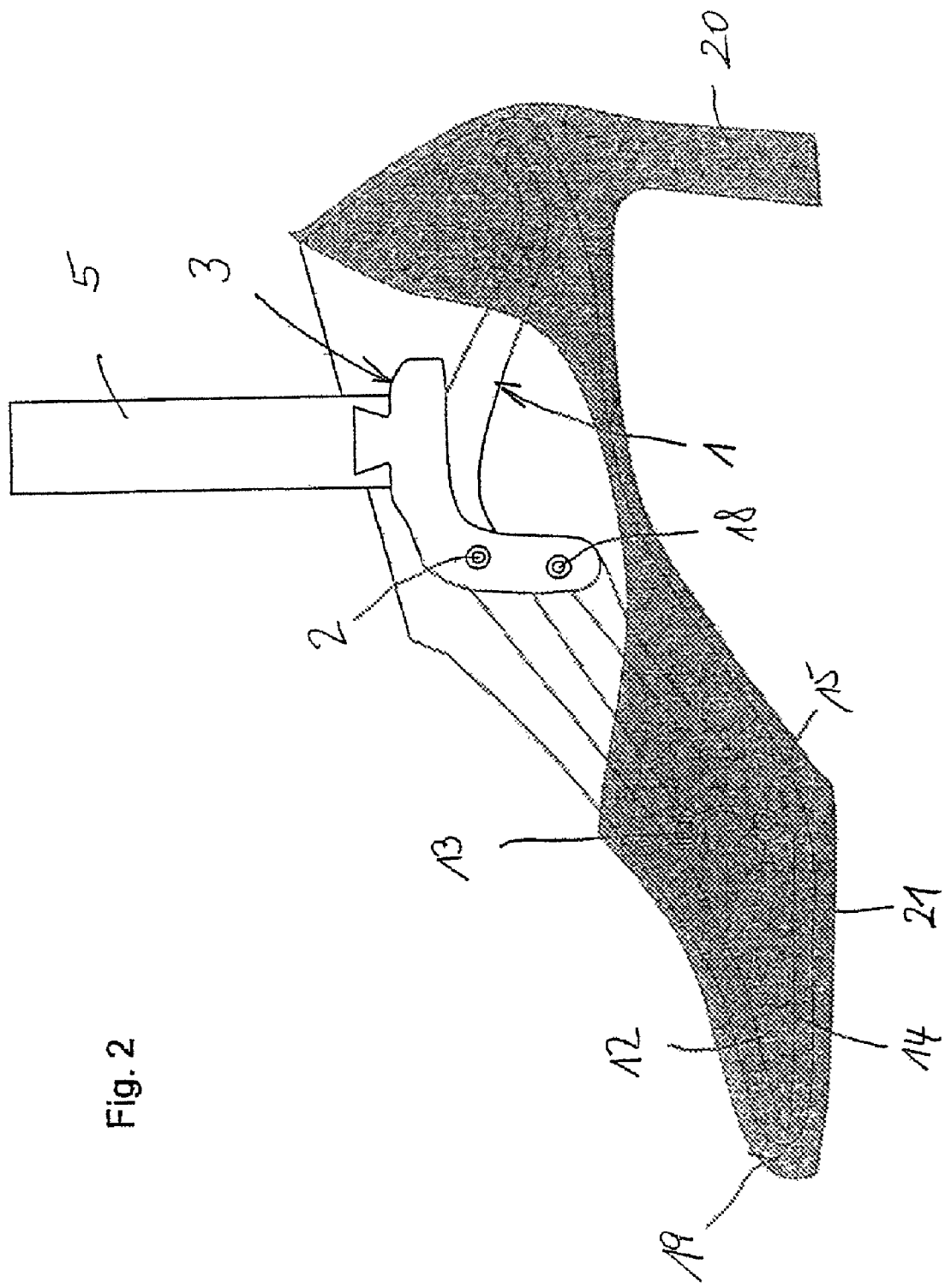
FIG. 2 shows a schematic view of the foot according to FIG. 1, in a shoe with a high heel.

The artificial foot is shown in FIG. 1 in the barefoot state, i.e. without the heel of a shoe. Compared to this, FIG. 2 shows the foot according to FIG. 1 in a shoe 19 that has a high heel 20. Accordingly, the connecting part 3 or lower leg part 5 is tilted rearward relative to the base foot part 1, as a result of which the forefoot part 12 is swiveled upward relative to the base foot part 1 via the articulated connection comprising joints 2, 13, 15, 18. Since the base foot part 1 in the shoe 19 is directed obliquely forward and downward because of the high heel 20, the upward swiveling of the forefoot part 12 is set such that the underside 14 of the forefoot part 12 extends parallel to the sole 21 of the shoe 19. The articulated connection shown thus ensures automatic adjustment of the foot to the height of the heel 20 with the aid of the swiveling movement of the forefoot part 12 by means of the articulated connection at the pivot joints 2, 13, 15, 18.

Figure 3:
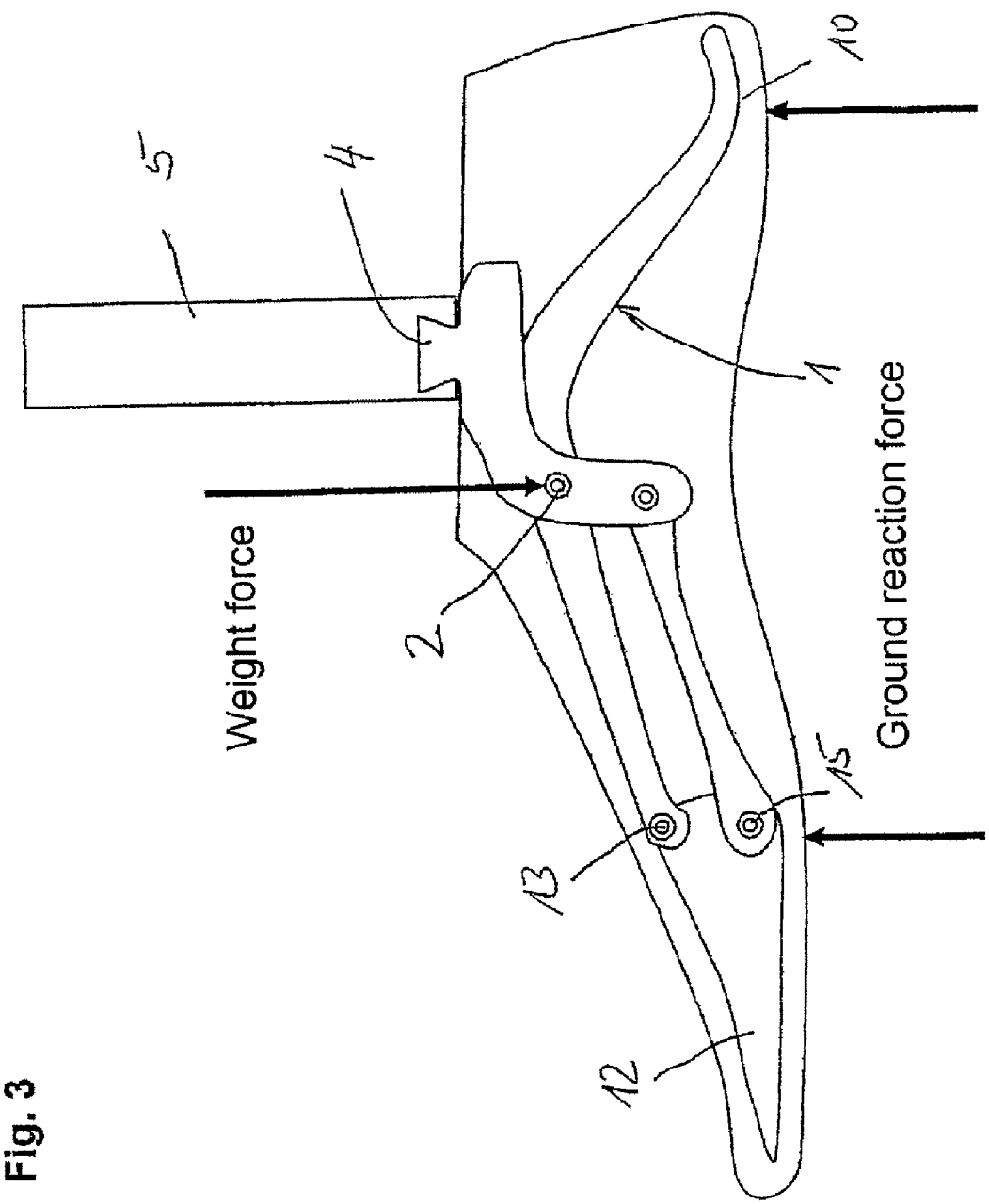
FIG. 3 shows a view according to FIG. 1, illustrating the position of the ankle joint.
Figure 4:
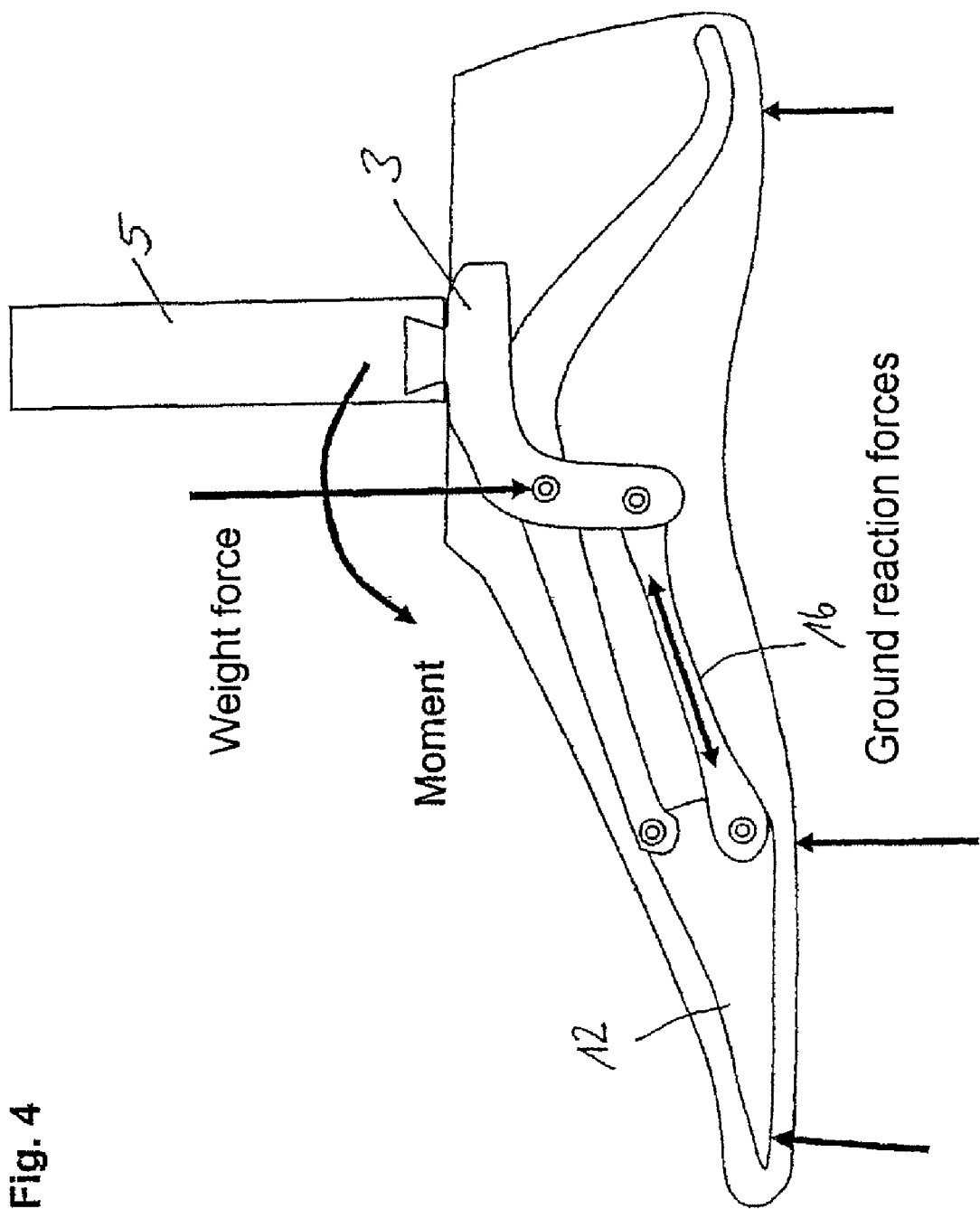
FIG. 4 shows a view according to FIG. 3, for a forwardly shifted load when standing.

FIGS. 3 and 4 illustrate the forces taken up by the foot according to the invention. The weight force is introduced directly into the ankle joint 2. The ankle joint 2 is positioned at a distance forward of the adapter attachment 4 and below-knee prosthesis 5, as a result of which the ankle joint 2 engages approximately centrally on the base foot part 1 which is articulated as a rocker on the ankle joint 2. The ground reaction forces are introduced in the area of the heel contact surface 10 and in the area of the ball of the foot, that is to say approximately level with the pivot joints 13, 15 of the forefoot part 12. Accordingly, the ground reaction forces are located more or less symmetrically to either side of the introduced weight force when there is a stable stance in equilibrium.

If the weight is now shifted forward in accordance with FIG. 4, a torque arises on the lower leg part 5 and connecting part 3 in the direction of the curved arrow in FIG. 4. In this way, a tensile force is exerted on the linking rod 16 in a rearward direction, as a result of which the front tip of the forefoot part 12 is pressed downward. The tip is therefore in a position to take up additional ground reaction forces, as is indicated in FIG. 4 by the additional arrow in the area of the tip of the forefoot part 12. The ground reaction force acting on the heel contact surface 10 has in this case decreased as a result of the forward shift in weight.

Figure 5:
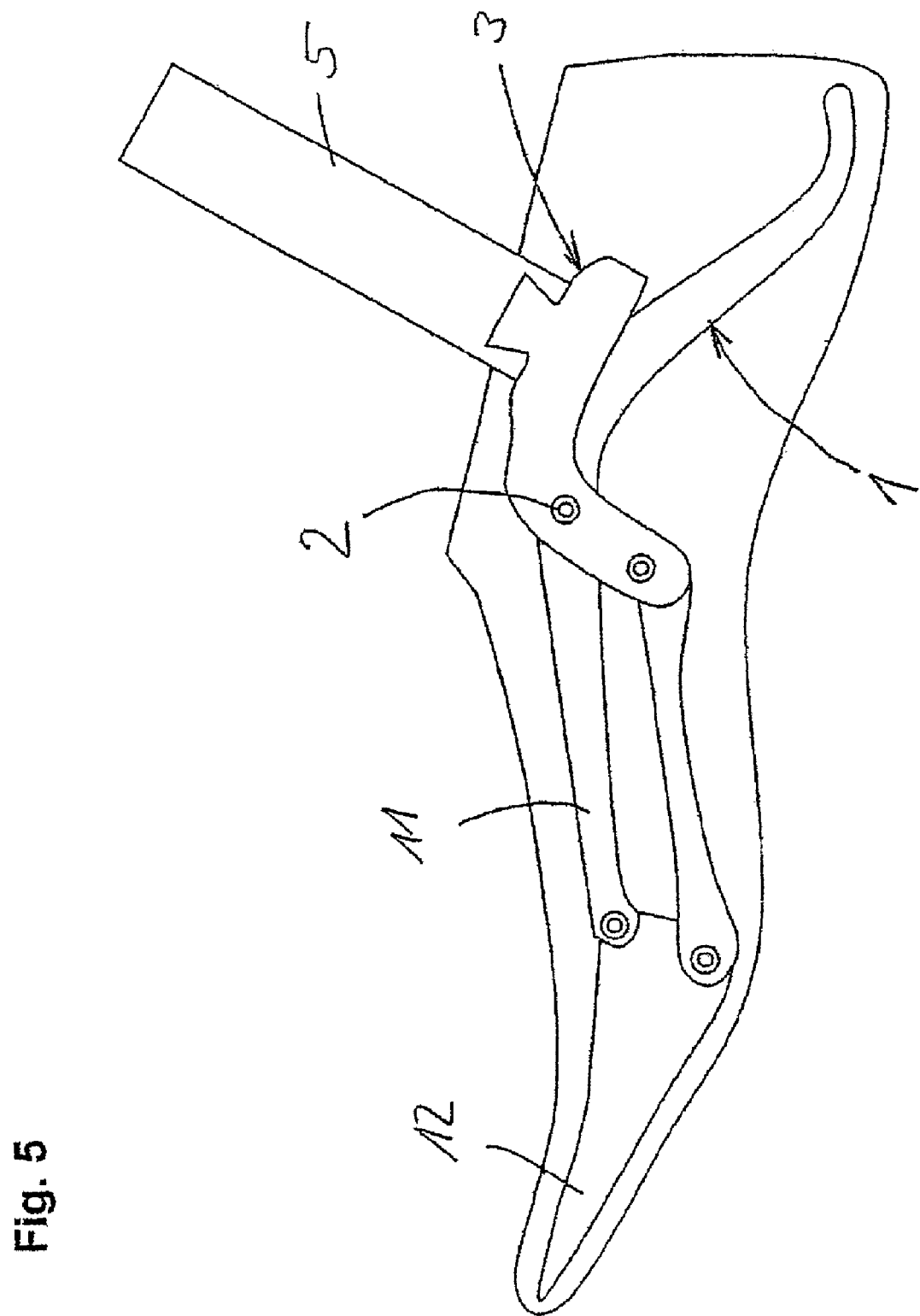
FIG. 5 shows a view of the foot according to FIG. 1 during walking, when the heel touches down.

FIG. 5 shows the foot according to FIG. 1 in a heel touch-down phase during walking. In this case, the lower leg part 5 or connecting part 3 is tilted rearward relative to the base foot part 1, so that the forefoot part 12 has been swiveled upward slightly, in an anatomically correct manner. When the foot is set down in the heel area, the rocker forming the base foot part 1 swivels abruptly downward with the midfoot section 11 around the ankle joint 2, so that the rearward swivel angle of the lower leg part 5 relative to the base foot part 1 is increased further, as a result of which the forefoot part 12 is swiveled upward to an extreme degree.

Figure 6:
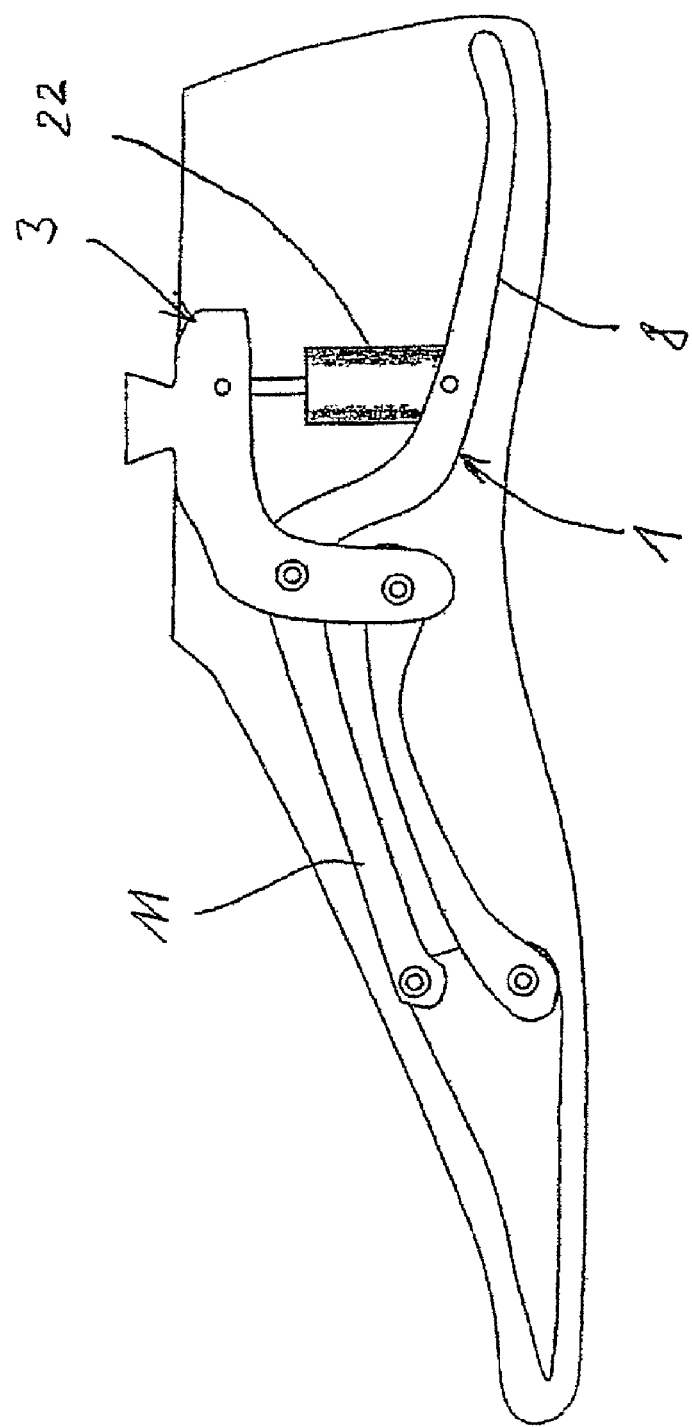
FIG. 6 shows a schematic view of a variant of the foot according to FIG. 1, corresponding to a second illustrative embodiment.

It may therefore be expedient, according to FIG. 6, to attenuate the swiveling of the base foot part 1 at heel touch-down by inserting a damper 22, for example in the form of a hydraulic damper, between the heel section 8 of the base foot part 1 and the connecting part 3. The elastic damper prevents the midfoot section 11 from dropping down in an undamped manner when the heel touches down.

Figure 7:
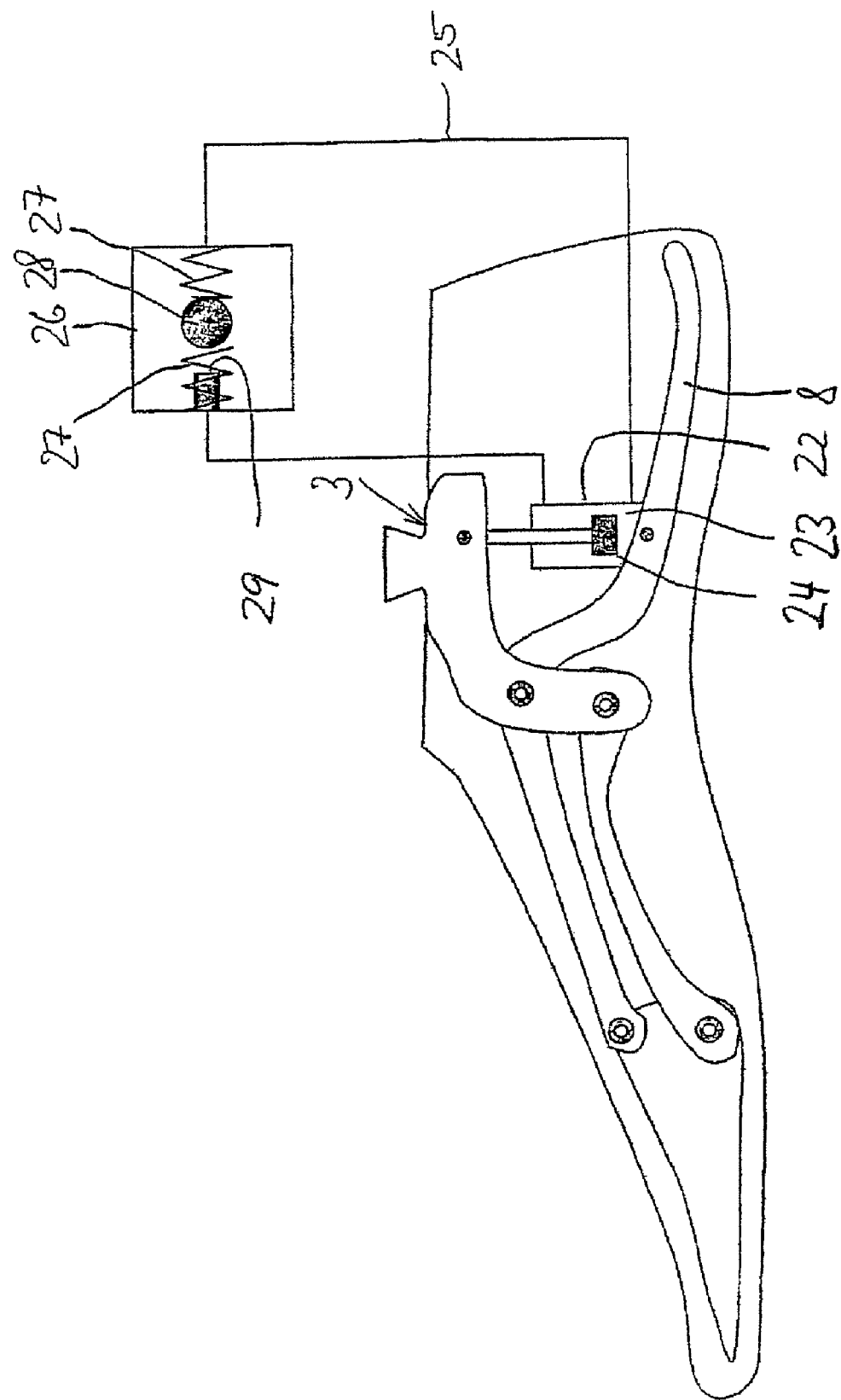
FIG. 7 shows a schematic view of a possible mode of action of a damper.

FIG. 7 illustrates a preferred mode of action of the damper 22. The latter is made up of a cylinder chamber 23 and of a piston 24. The relative movement between heel section 8 and connecting part 3 is damped via a circuit line 25 through which the hydraulic fluid has to flow from one side to the other side of the piston 24. A valve arrangement 26, shown schematically here and consisting of a shut-off ball 28 held by springs 27, is preferably inserted into the circuit line 25. At a low flow velocity of the hydraulic fluid in the circuit line 25, as occurs for example in a quasi-static state for adaptation to the different heights of a heel 20 of a shoe, the required distance compensation takes place in damped form by means of the hydraulic fluid.

In the event of a momentary load peak, as occurs when the heel touches down during walking, the ball 28 is pressed against a shut-off surface 29 by the high flow velocity and blocks the flow path for the hydraulic fluid. In this case, the heel touch-down does not lead to a change in the spacing adjustment, effected by the hydraulic cylinder 22, between the heel section 8 and the connecting part 3.

In order to permit an elastic touch-down of the heel, it is expedient for an elastic member, for example a spring, to be coupled in series with the damper 22.

Figure 8:
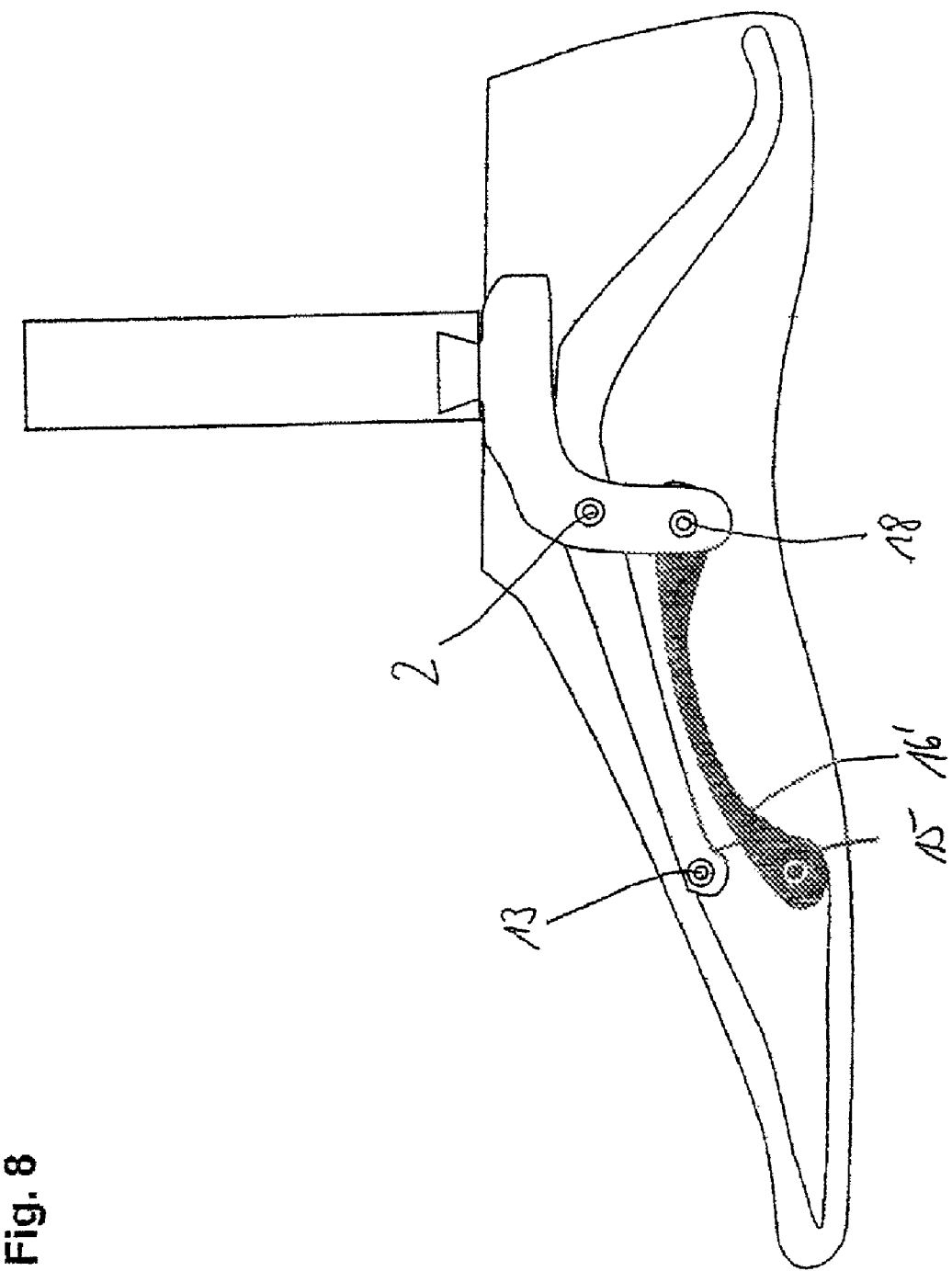
FIG. 8 shows a third embodiment of a foot according to the invention with an elastic linking rod, in the rest state.
Figure 9:
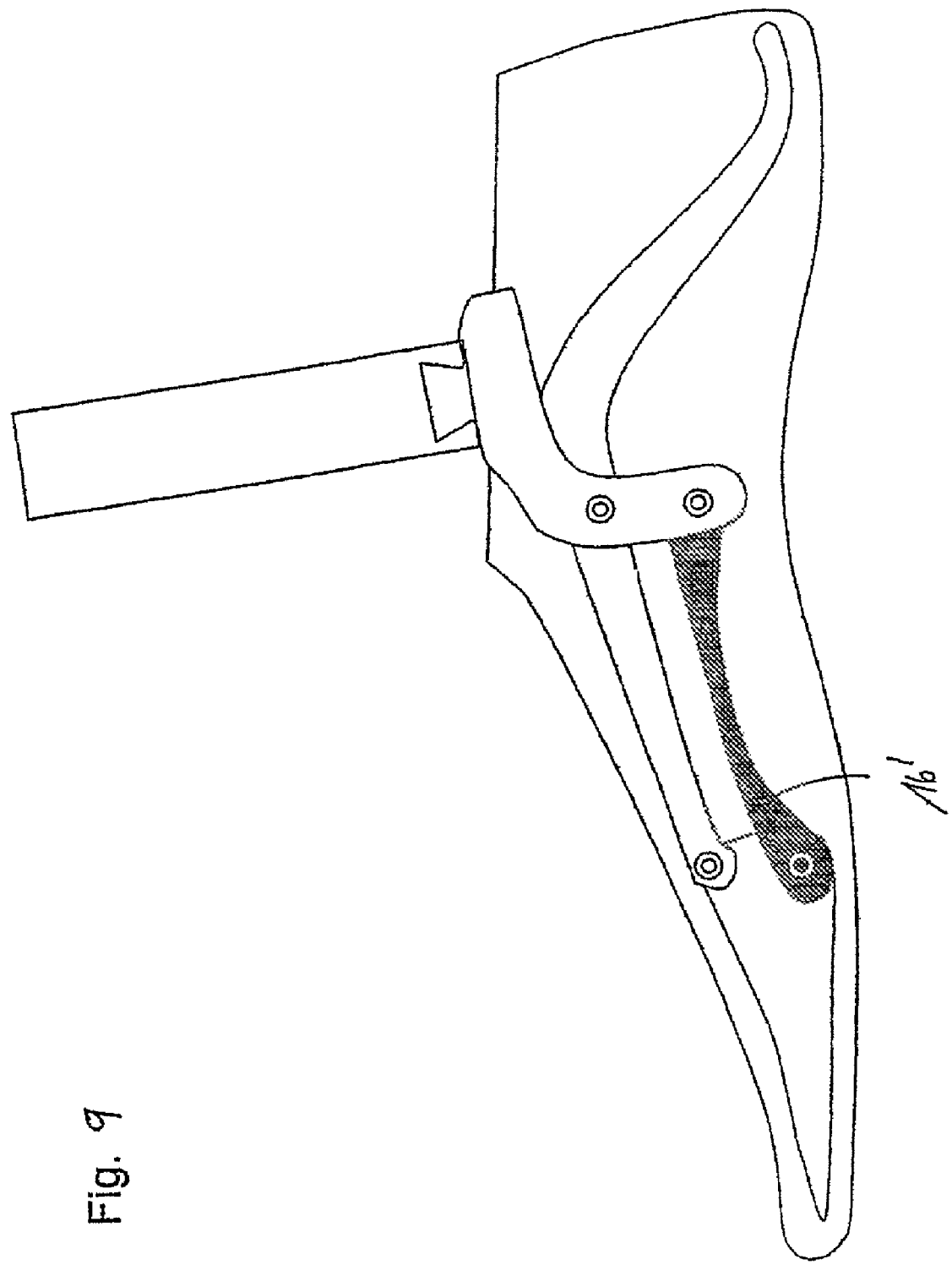
FIG. 9 shows a view according to FIG. 8, for a heel-to-toe movement across the forefoot.

The embodiment shown in FIGS. 8 and 9 entails the same arrangement of the pivot joints 2, 13, 15, 18, but with the difference that the linking rod 16' between the pivot joints 15 and 18 is formed by a curved leaf spring. FIG. 8 shows the state when the person is standing steady. When the weight is shifted forward, the rigid linking rod 16 according to FIG. 1 would cause an immediate and considerable loading of the forefoot, which would not correspond to the natural feeling when standing. When the weight is shifted forward according to FIG. 9, the linking rod 16' can, by contrast, lengthen slightly through elasticity, so that, with a further tensile force on the linking rod 16', it provides a progressively increasing counter-force for the forefoot. A certain "swaying", when the patient is standing, is thus stabilized by an elastic, gradually increasing counterforce, which corresponds to the natural feeling when standing.

Figure 10:
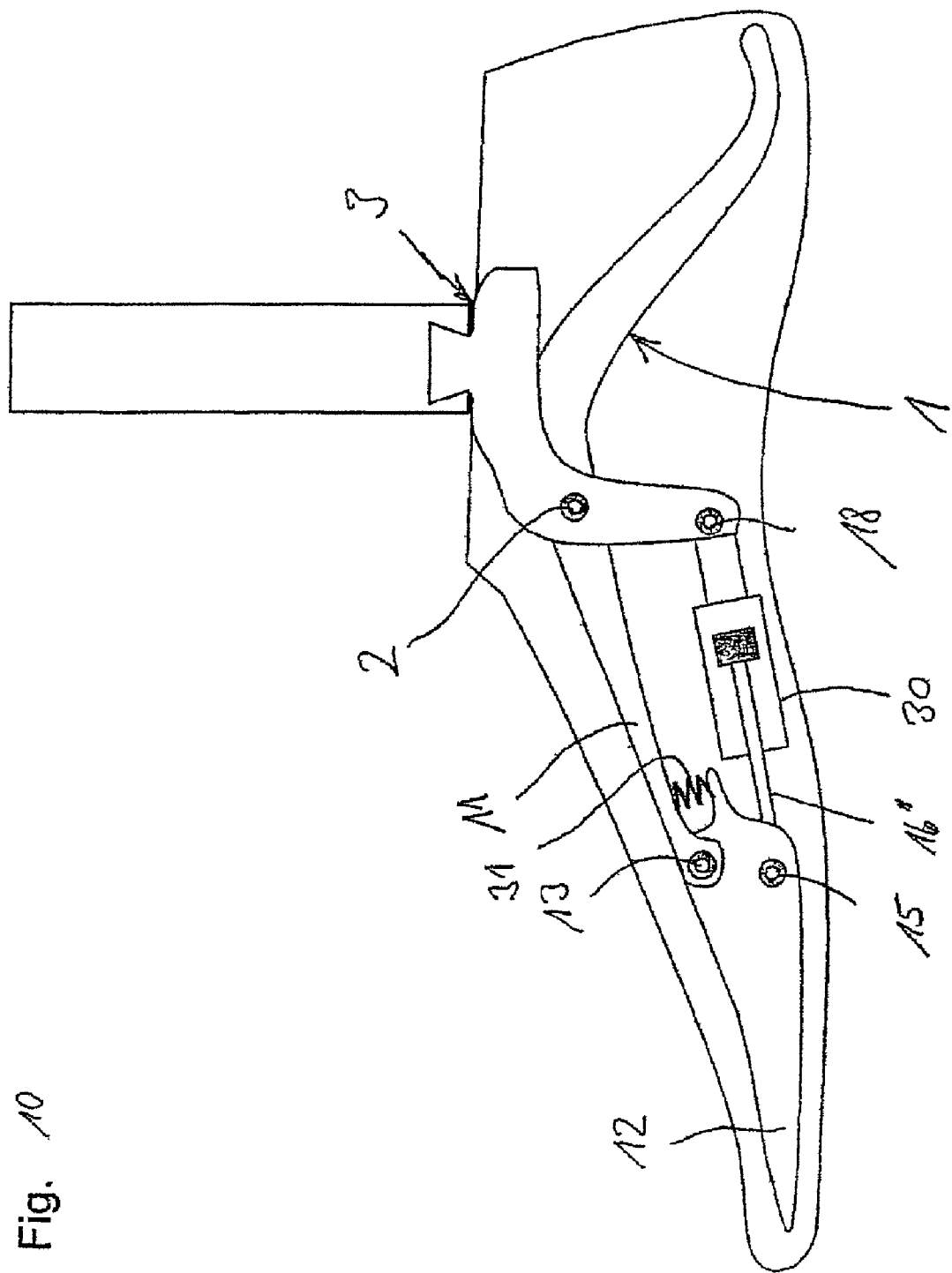
FIG. 10 shows a fourth embodiment of the foot according to the invention, with a length-adjustable linking rod.

FIG. 10 shows an embodiment of the artificial foot in which the linking rod 16" is designed to be adjustable in length by means of a hydraulic cylinder 30. Like the hydraulic cylinder 22 in FIG. 7, the hydraulic cylinder 30 in this case can, in the event of a momentary load, delay a damping of the transmission of the angular position of the connecting part 3 relative to the base foot part 1 to the angular position of the forefoot part 12 relative to the base foot part 1. By means of the change of length of the hydraulic cylinder 30, the transmission ratio of the parallelogram linkage between the connecting part 3 and the forefoot part 12 can be changed such that excessive downward pressing of the foot part 12 is avoided at a forwardly inclined angular position of the connecting part 3 relative to the base foot part during heel-to-toe movement. A direct transmission of the angular position would lead to a "digging in" of the toe area of the forefoot part 12 during the heel-to-toe movement across the forefoot part 12. This digging-in effect can be avoided by virtue of a change in the transmission ratio between connecting part 3 and foot part 12, brought about by the change in length of the hydraulic cylinder 30. Arranged between the forefoot part 12 and the midfoot section 11 of the base foot part 1 there is a spring 31 which defines a preferred position of the forefoot element. The spring 31 can advantageously be replaced by a spring/damper combination arranged in series.

Figure 11:
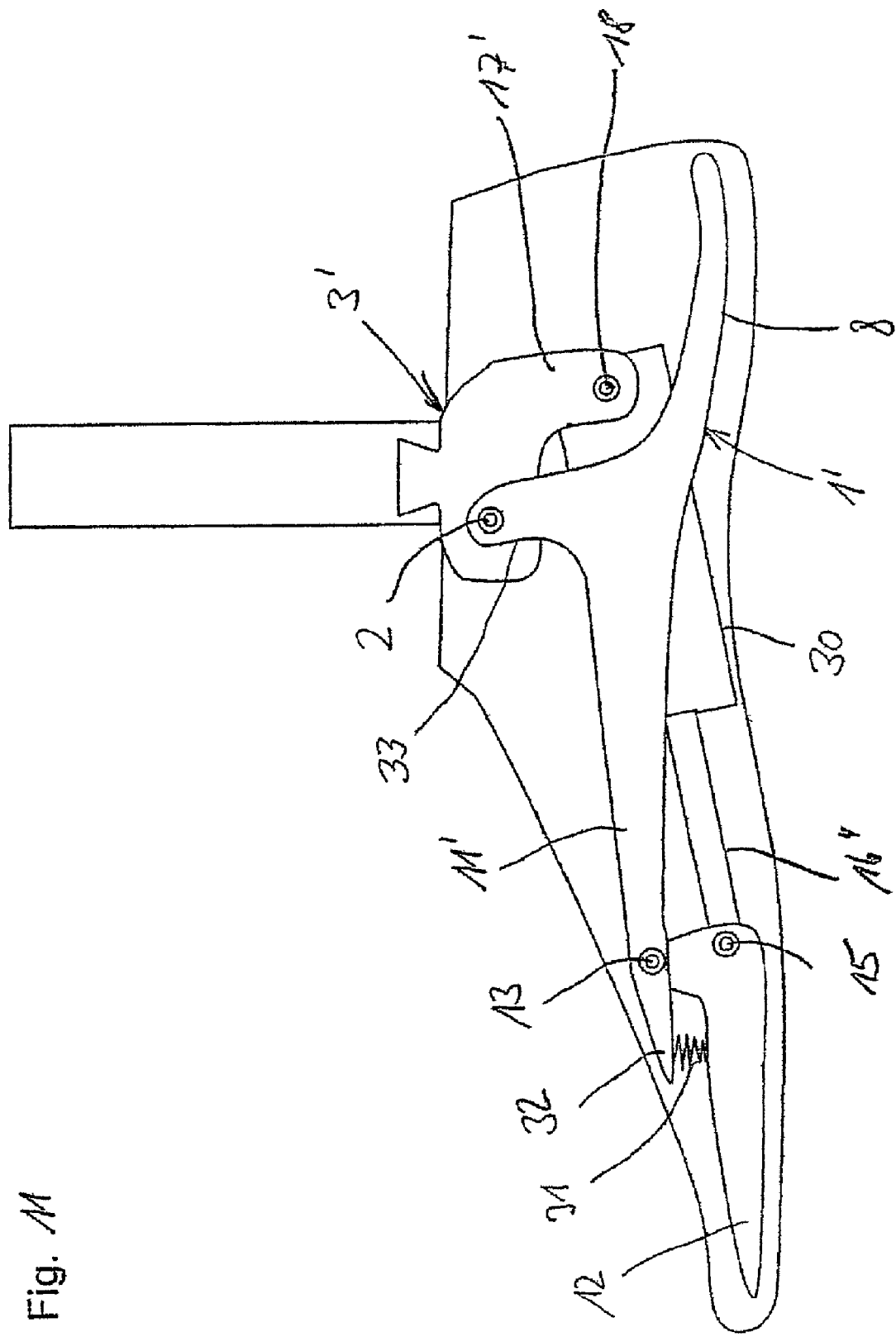
FIG. 11 shows a fifth embodiment as a design variant to the embodiment according to FIG. 10.

FIG. 11 shows an embodiment having the same action as the embodiment according to FIG. 10, but with structural modifications. Thus, the base foot part 1' extends from the heel area 8 curved only slightly upward into the midfoot section 11'. The midfoot section 11' has an extension piece 32 which protrudes past the pivot joint 13 and carries the spring 31 or spring/damper combination acting on the forefoot part 12.

The connecting part 3' is again approximately L-shaped, but the downward extension piece 17' is now arranged at the rear end, as a result of which the pivot joint 18 is shifted rearward in the direction of the heel area. A longer travel is therefore available for the linking rod 16" with the hydraulic damper 30.

The base foot part 1' is articulated on the ankle joint 2 via an upward extension piece 33 of the base foot part 1'.

Figure 12:
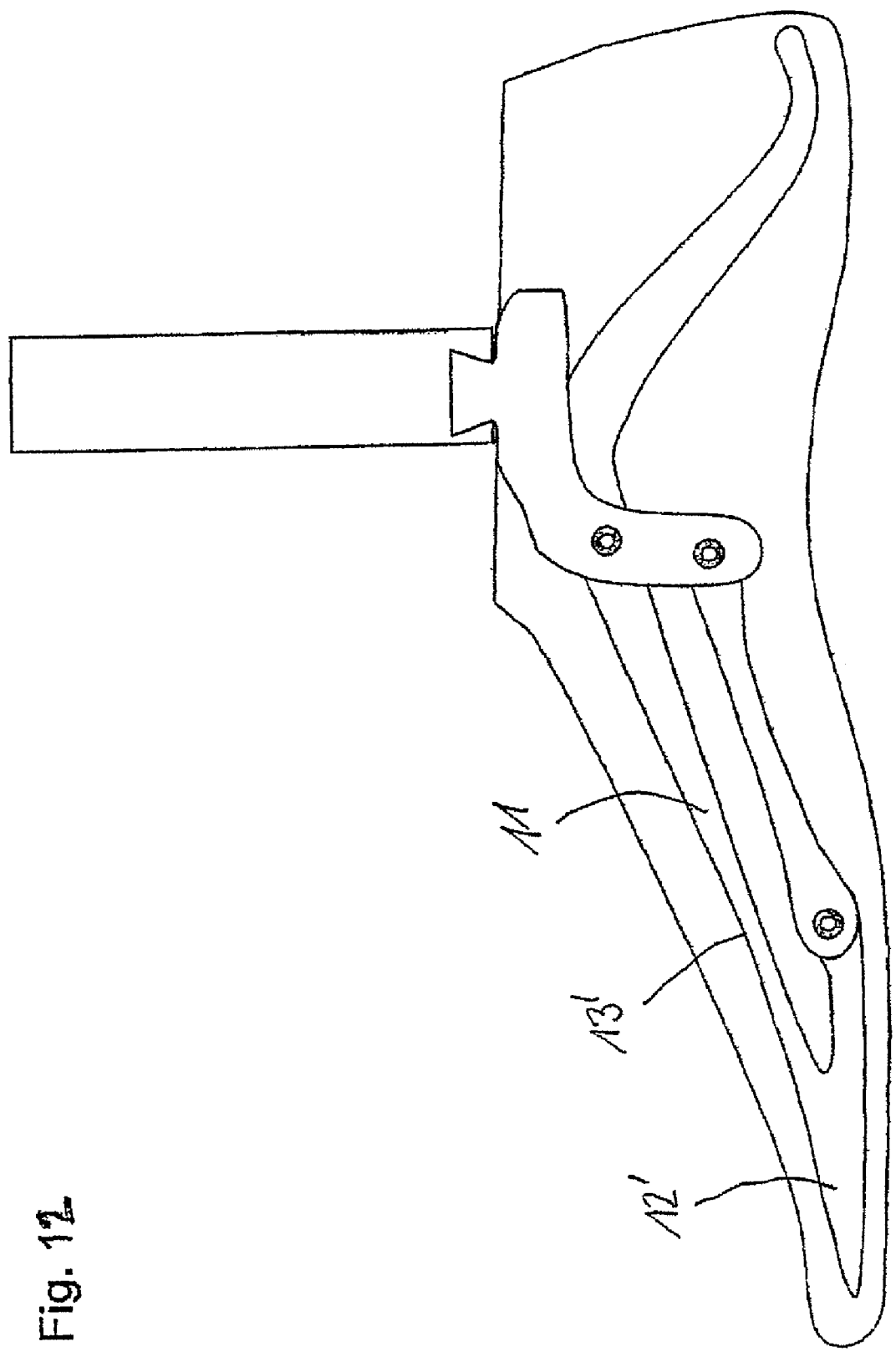
FIG. 12 shows a sixth embodiment with an articulated arrangement comprising a joint in the manner of a hinge joint.

The embodiment shown in FIG. 12 corresponds substantially to the embodiment according to FIG. 1, the only difference being that the pivot joint 13 is omitted and is replaced by a flexible section 13' of the midfoot section 11, which thus merges into the forefoot part 12' via the flexible section 13' formed by tapering of the material. Of course, the embodiment with the joint 13' can be combined with the variants shown in the other figures of the drawing, for example with a flexible linking rod 16' or with a length-adjustable linking rod 16".

The invention claimed is:

1. An artificial foot comprising:
   a connecting part for establishing a connection to a lower leg part;
   a base foot part pivotably connected to the connecting part via an ankle joint, wherein said base foot part includes a heel section which extends rearward of the ankle joint and a midfoot section which extends forward of the ankle joint;
   a linking rod pivotably connected to the connecting part and extending forward of the ankle joint;
   a forefoot part, said forefoot part either being pivotably connected to the midfoot section of the base foot part or connected to the midfoot section of the base foot part by a flexible connection region effectively forming a hinged connection, and said forefoot part being pivotably connected to the linking rod,
   wherein said midfoot section and said linking rod being configured to form an articulated connection with said connecting part and said forefoot part that during a walking process transmits an angular position of the connecting part relative to the base foot part in a proportional manner to an angular position of the forefoot part relative to the base foot part so that a change in the angular position of the connecting part in a rearward direction leads to a proportional lifting of the forefoot part and the forefoot part is pressed downward if the connecting part is tilted forward relative to the base foot part,
   wherein the articulated connection is a four-joint arrangement which includes said connecting part, said midfoot section, said linking rod, and said forefoot part, wherein a length of either said midfoot section or said linking rod between said connecting part and said forefoot part in said articulated connection is adjustable, and
   wherein said four-joint arrangement is configured such that during the walking process when the artificial foot rolls forward across the forefoot part, a digging in of the forefoot part is avoided by allowing a change of said length between said connecting part and said forefoot part in said articulated connection so as to reduce a transmission factor of the angular positions of the connecting part and the forefoot part.

2. The artificial foot as claimed in claim 1, wherein the midfoot section and the linking rod are arranged substantially parallel to one another.

3. The artificial foot as claimed in claim 1 wherein the connecting part has an extension piece which extends downward across the ankle joint.

4. The artificial foot as claimed in claim 1 wherein the forefoot part is pivotably connected to the midfoot section of the base foot part.

5. The artificial foot as claimed in claim 1 wherein the length of the linking rod is adjustable such that the linking rod is elastically deformable in a longitudinal direction.

6. The artificial foot as claimed in claim 1 wherein the linking rod is configured in the articulated connection to be subjected mainly to tensile loading.

7. The artificial foot as claimed in claim 1 further comprising at least one sensor that detects parameters related to walking or standing.

8. The artificial foot as claimed in claim 1 wherein the length of the linking rod is adjustable, and there is a hydraulic cylinder in said linking rod.

9. The artificial foot as claimed in claim 1 further comprising an elastic member positioned between said forefoot part and said base foot part.

10. The artificial foot as claimed in claim 1 wherein a spring/damper combination is positioned between said forefoot part and base foot part wherein the linking rod comprises the spring/damper combination, which is adjustable in length.

11. The artificial foot as claimed in claim 1 wherein a spacing between joints on the forefoot part is smaller than a spacing between joints on the connecting part.

12. The artificial foot as claimed in claim 1 wherein the ankle joint is arranged at a distance forward of a connection point between the connecting part and the lower leg part.

13. An artificial foot comprising:
    a connecting part for establishing a connection to a lower leg part;
    a base foot part pivotably connected to the connecting part via an ankle joint, wherein said base foot part includes a heel section which extends rearward of the ankle joint and a midfoot section which extends forward of the ankle joint;
    a linking rod pivotably connected to the connecting part and extending forward of the ankle joint;
    a forefoot part, said forefoot part either being pivotably connected to the midfoot section of the base foot part or connected to the midfoot section of the base foot part by a flexible connection region effectively forming a hinged connection, and said forefoot part being pivotably connected to the linking rod; and
    an adjustment element arranged between said base foot part and said connecting part, wherein said adjustment element provides an adjusting action that comes into effect only when there is a load that continues over several seconds,
    wherein said midfoot section and said linking rod being configured to form an articulated connection with said connecting part, and said forefoot part that during a walking process transmits an angular position of the connecting part relative to the base foot part in a proportional manner to an angular position of the forefoot part relative to the base foot part so that a change in the angular position of the connecting part in a rearward direction leads to a proportional lifting of the forefoot part and the forefoot part is pressed downward if the connecting part is tilted forward relative to the base foot part, and
    wherein the articulated connection is a four-joint arrangement which includes said connecting part, said midfoot section, said linking rod, and said forefoot part.

14. The artificial foot as claimed in claim 13 wherein the adjustment element includes a hydraulic cylinder.

15. The artificial foot as claimed in claim 14 wherein said adjustment element includes a valve arrangement inserted into a circuit line in which hydraulic fluid flows from one side to an other side of a piston of the hydraulic cylinder, wherein said valve arrangement blocks the circuit line when a predetermined flow velocity is exceeded.

16. The artificial foot as claimed in claim 13 wherein the adjustment element is combined with an elastic member that can be deformed by momentary loads.

* * * * *